United States Patent
Walker

[11] Patent Number: 5,383,891
[45] Date of Patent: Jan. 24, 1995

[54] NOSE BLEED KID

[76] Inventor: Marshall D. Walker, 10238 Alamo Ct., Wichita, Kans. 67212

[21] Appl. No.: 114,451

[22] Filed: Aug. 31, 1993

Related U.S. Application Data

[63] Continuation-in-part of Ser. No. 681,350, Apr. 8, 1991, abandoned.

[51] Int. Cl.⁶ .................. A61M 29/00; A61M 31/00; B65D 69/00; A61F 13/15
[52] U.S. Cl. .................. 606/196; 606/199; 206/570; 206/438; 206/803; 206/828; 604/57; 604/285; 604/363; 604/369; 604/374; 604/904
[58] Field of Search ........ 206/570, 803, 828, 438–440; 128/DIG. 22, 114.1, 858; 604/1–3, 12, 54, 57, 285–288, 309, 363, 369, 374, 904; 606/191–192, 195–196, 198–199; 602/17, 74

[56] References Cited

U.S. PATENT DOCUMENTS

| | | | |
|---|---|---|---|
| 1,051,850 | 1/1973 | Sandmark | 606/196 |
| 1,732,697 | 1/1929 | Ryan | |
| 2,490,168 | 12/1949 | Strauss | 664/2 |
| 3,884,241 | 5/1975 | Walker | 606/199 |
| 4,030,504 | 6/1977 | Doyle | 606/199 |
| 4,338,941 | 7/1982 | Payton | 128/325 |
| 4,363,319 | 12/1982 | Altshuler | 206/570 |
| 4,457,756 | 7/1984 | Korn et al. | 604/386 |
| 4,534,342 | 8/1985 | Paxa | 602/74 |
| 4,568,326 | 2/1986 | Rangaswamy | 606/199 |
| 4,592,357 | 6/1986 | Ersek | 606/194 |
| 4,646,739 | 3/1987 | Doyle | 606/199 |
| 4,895,559 | 1/1990 | Shippert | 604/904 |
| 4,950,280 | 8/1990 | Brennan | 604/1 |

*Primary Examiner*—Randall L. Green
*Assistant Examiner*—K. M. Reichle
*Attorney, Agent, or Firm*—Edward L. Brown, Jr.

[57] ABSTRACT

A hemostatic tampon kit including an oval-shaped tampon adopted for easy insertion into the nasal cavity by a layman, composed of a compressed synthetic sponge adapted to expand upon contact with an aqueous fluid, the tampon includes a string attached thereto for anchoring to a nasal bandage placed over the nostrils of the user which includes an absorbent drip pad and an attachment element on the bandage for engaging and holding the tampon string. A sealable container of liquid vasoconstrictive medication for wetting and expanding the tampon and a container of anti-bacterial ointment for lubricating the tampon during insertion.

5 Claims, 2 Drawing Sheets

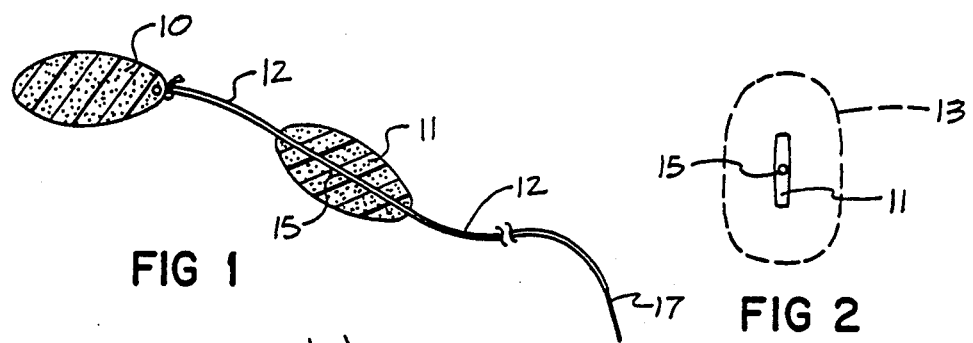
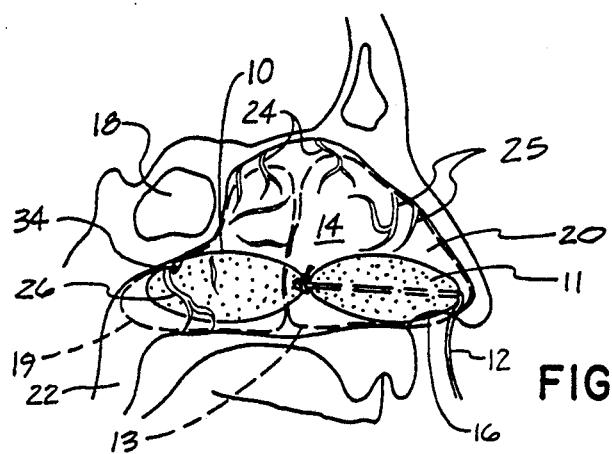
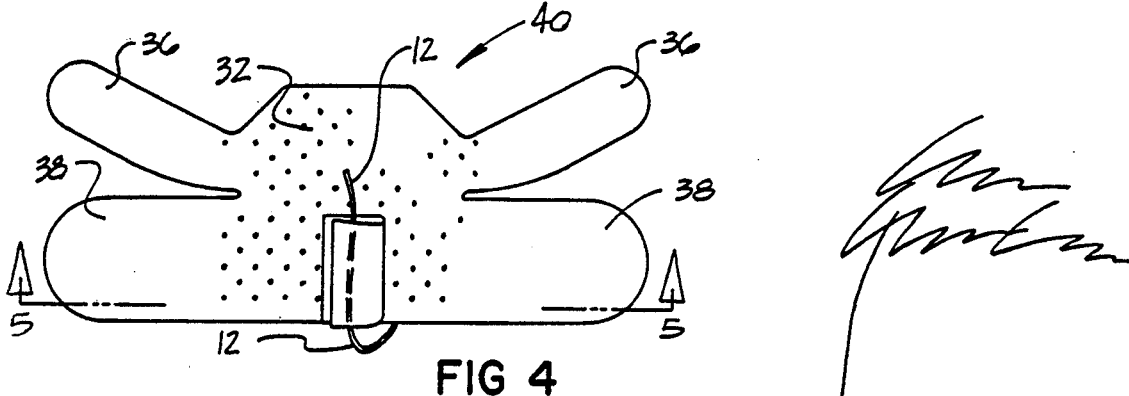
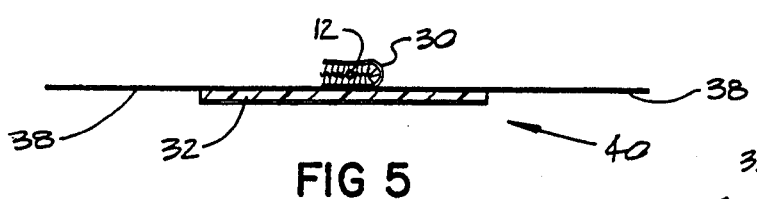
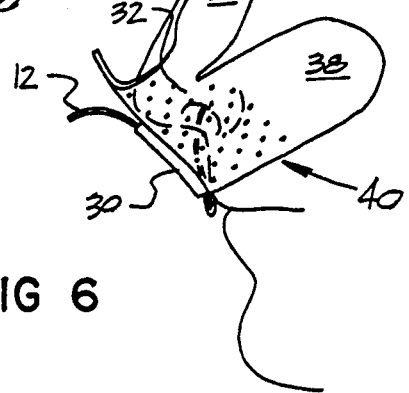

NOSE BLEED KID

This is a continuation-in-part application of prior co-pending patent application Ser. No. 07/681,350 filed Apr. 8, 1991, and now abandoned entitled NOSE BLEED KIT, the inventor being Marshall D. Walker.

BACKGROUND OF THE INVENTION

This invention relates generally to the treatment of nasal hemorrhages or nose bleeds, and more particularly to a kit and apparatus for providing hemostatic pressure to the various areas of the nasal cavity which commonly hemorrhage.

Nasal hemorrhaging which requires packing of the nose is a common phenomenon since branches of several major arteries are located quite close to the surfaces of the nasal septum and other areas of the nasal cavity. One of the more common methods of arresting such bleeding is to chemically cauterize the area of the vascular plexus and then insert absorbent packing materials such as gauze or cotton into the nasal cavity.

As in most types of bleeding, the direct application of pressure to the bleeding area in various forms has been very successful. One method of achieving this pressure has been through the use of inflatable devices such as Sandmark U.S. Pat. No. 1,051,850 and Payton U.S. Pat. No. 4,338,941.

Another method of applying pressure to the bleeding vessels is the use of a spring-type wire clip as taught by Kern U.S. Pat. No. 4,457,756, wherein spring pressure is applied to a packing placed just inside the nostrils to handle an anterior hemorrhage. A large percentage of all nose bleeds in the order of 90%, occur within the location of the vascular plexus which is located in the forward areas of the nasal cavity on the nasal septum or nasal partition. The various networks of arteries, minute blood vessels and capillaries in this area are the most common source of nose bleeds or nasal hemorrhages.

There are various home remedies for simple nose bleeds such as cold compresses to the neck, manually compressing the nostrils along with various other techniques, none of which are particularly effective since the actual site of the bleeding is within the nasal cavity.

Nose bleeds in this forward area of the vascular plexus commonly referred to as the Kiesselbach plexus, are relatively easy to treat by a non-physician because of their ready accessibility and the bleeding area can be visually ascertained. Nasal hemorrhaging further back in the nasal cavity presents more difficult problems which the laymen cannot treat since the source of the bleeding is difficult to ascertain and difficult to properly pack or apply pressure thereto.

Applying pressure to hemorrhaging vessels through the use of an expandable sponge through wetting was taught by Ryan U.S. Pat. No. 1,732,697. This patent also taught the use of a lubricant on the sponge to assist in insertion.

Various forms of vasoconstrictive agents have been used over the years such as taught in Kern, mentioned above, by placing the agents on absorbent pads spring-biased against the bleeding vessels.

More recent expandable sponge designs were taught by Doyle in U.S. Pat. Nos. 4,030,504 and 4,646,739. The '504 Doyle patent requires rather precise positions to achieve its FIG. 1 position and therefore its claim of use by an untrained medical person is questioned. The '739 Doyle patent is supposedly usable by non-medically trained individuals, however, it has never been sold over the counter for laymen use.

On the market today there are a variety of expandable sponge nasal tampons available, however, their use is strictly limited to physicians and special equipment is required for insertion.

While certain of the above-mentioned patents are described as first-aid or home-use applications, there currently is no home-use product on the market which is effective in controlling nose bleeds.

SUMMARY OF THE INVENTION

The present invention is a pre-packaged nose bleed kit sold across the counter for home use which also can be used by physicians in the treatment of acute epistaxis, as well as the common nose bleed. The kit includes a hemostatic tampon construction of a compressed synthetic hydrocellulose sponge material which expands upon wetting and is oval in shape with a pull string attached to one end thereof for easy insertion, retention and removal from the nasal cavity. The kit may further include a nasal bandage which provides an absorbent drip pad under the nostrils and a hook and loop plastic fastening material strip for anchoring the tampon pull string. Another form of anchoring the tampon string would be some form of adhesive strip attached to the cheek. The kit also includes a sealable container of a liquid vasoconstrictive agent for wetting and expanding the sponge and a sealable container of anti-bacterial ointment for lubricating the sponge during insertion and for inhibiting bacterial growth. A graduated kit would include additional like-shaped tampons with a longitudinal passage therethrough which can be threaded by the pull string of the first tampon to provide a graduated length of sponge depending upon the particular location of the nose bleed in the nasal cavity. The invention also discloses a new tampon construction having a thin releasable sheet of collagen fiber material surrounding the tampon which readily releases from the tampon upon contact with an aqueous solution. The particular design of the tampon and method for attachment of the collagen material is also unique.

It is therefore the principal object of the present invention to provide a self-contained home-use nose bleed kit which is effective, safe and requires no special instruments or expertise in its use.

A further object of the present invention is to provide a hemostatic tampon construction in combination with coagulating fibers to produce a more effective blood coagulant means.

Another object of the present invention is to provide a hemostatic tampon which is graduated in length and anchored to an exterior location so as to prevent movement once in place.

This and other objects and advantages of the invention will become apparent from the following description, and accompanying drawings and the appended claims.

BRIEF DESCRIPTION OF THE DRAWINGS

FIG. 1 is a side elevational view, partly in section of the hemostatic tampon and its attendant pull string with a second tampon threaded on the pull string;

FIG. 2 is an end view of the compressed tampon with a dotted line showing of its expanded shape;

FIG. 3 is a cross sectional elevational view through the nasal cavity showing the positioned tampons, nasal wall and some of the major arteries;

FIG. 4 is a plan view of the nasal bandage with the tampon string attached thereto;

FIG. 5 is a sectional view taken along line 5—5 of FIG. 4;

FIG. 6 is a side profile view of a patient with the nasal bandage partly in place.

DESCRIPTION OF THE PREFERRED EMBODIMENT

Figure 7:
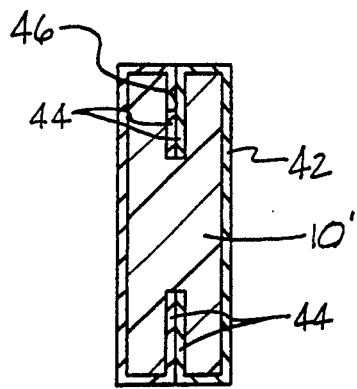
FIG. 7 is a sectional view of a modified form of nasal hemostatic tampon in its compressed state.

Referring now to FIGS. 1 and 2, the basic hemostatic tampon 10 is shown in plan form having a substantially oval shape with a pull string 12 sewn to one end of the tampon. The tampon is composed of a compressed surgical sponge material which when wetted expands from its solid line showing in FIG. 2 to the dotted line cross sections 13 and 19, shown in FIGS. 2 and 3. The tampon 11 or 10 is between 3 to 5 cm in length and between 2 to 3 mm thick, and between 15 to 25 mm in width. In its compressed form it is uniform in thickness, as can be seen in FIG. 2, when wetted it will expand more in thickness than in length and width. Tampon 10 includes a pull string 12 tied to one end, and the additional tampons 11 include a longitudinal passage 15 therethrough for receipt of string 12. When it is desirous to have a tampon of increased length, additional tampons 11 are threaded onto pull string 12 which has a hardened tip 17 to assist in passing through passage 15. While the tampon string enhances the ability to remove the tampon, its primary purpose is to anchor the tampon or tampons in place.

The material utilized in string 12 can be very soft and pliable loose fiber so as not to create an irritation around the nostril of the wearer. There are a variety of methods of attaching string 12 to tampon 10 such as sewing or tying it to one end, as illustrated, or passing the string longitudinally through the sponge and back so as to increase the anchoring surface of the string.

FIG. 3 illustrates a vertical sectional view through the nasal cavity 14 with two tampons 10 and 11 positioned therein. In their compressed form, as shown in solid line, the oval tampons are easily inserted within the nostril 16. To assist in insertion, an antibiotic ointment is placed on the tampon for lubrication, such as NEOSPORIN, a brand produced by Burrough Wellcome Co. When the tampons 10 and 11 are wetted with any type of aqueous solution as, for example, a vasoconstrictive medication, they will expand outwardly in all three dimensions against the septum on one side and the lateral wall 20 of the nasal cavity on the other to an approximate outline of the dotted lines 13 and 19. As shown in FIG. 3, the nasal cavity 14 is basically domed-shaped on the top having a contracted canal at the rear end of the nasal cavity directly below sinus cavity 18. Canal 34 in turn communicates with the pharynx 22. Due to the complex nature of the various recesses and protrusions in the nasal cavity 14, it is sometimes difficult to apply pressure to the various blood vessels contained within the nasal cavity. Positioned on the lateral outer wall 20 of the septum are branches 25 of the facial artery and the anterior ethmoidal artery. Also, in lateral wall 20 are additional artery branches 24 approximate the upper areas of the nasal cavity 14. Positioned in the rear areas of the nasal cavity in canal 44 are additional posterior septal branch arteries 26.

The most common area for nose bleeds to occur takes place in the area referred to as the Kiesselbach plexus which is located in the nasal cavity opposite the lateral outer wall 20 in the first 3 centimeters in from the nostrils 16. In viewing FIG. 3, the single tampon 11 sufficiently covers this Kiesselbach plexus area and therefore a single tampon rather than two, as illustrated, will be sufficient to stop those particular bleeding sites. Bleeding sites which are more posterior such as arteries 24 and 26 would not be reached by a single tampon and for that reason a double tampon 10 and 11, as shown in FIG. 3, would be required. This is achieved by threading the pull string 12 through passage 15 of second tampon 11 and inserting the connected double tampons into the nasal cavity 14 with the pull string extending out the nostril and anchored exteriorly. An alternate method would be to utilize two separate tampons 10, each having a separate pull string 12 wherein the first tampon 10 is positioned at its posterior site, as seen in FIG. 3, and then inserting the second tampon 10 immediately in front thereof with the two respective pull strings extending out of the nostril 16 and anchored to bandage 40. An alternate anchor means could be any form of adhesive strip such as the brand name COVERSTRIP II produced by Beiesdorf, Inc.

With the tampons 10 and 11 in place, the vasoconstrictive medication such as 1% neosynephrine is applied from a dropper dispenser 52 expanding the sponge. The expanded sponge holds the medication directly in contact with the bleeding site, therefore stimulating clotting.

After the tampons 10 and 11 are in place and expanded with their pull string 12 extending from the nostril, nasal bandage 40 is positioned under the nose, as shown in FIG. 6. The bandage 40 includes a thin sheet of stretchable plastic with adhesive-covered ends 38 attached to the upper lip on both sides thereof while adhesive-covered ends 36 are pulled upward for attachment to the respective sides of the nose. Positioned in the center of the bandage 40 is an absorbent pad 32 which includes multiple layers of gauze for absorption of the blood which may drip from the nostrils until clotting has occurred. Sewn to the outer surface of the bandage 40 is a piece of hook and loop plastic fastening material 30 which when folded in half retains the pull string 12 in tight engagement. Once the tampons 10 and 11 are properly positioned in the nasal cavity 14, the anchored pull string 12 prevents the tampons from migrating further back into the nose. The fastening means 30 also keeps the string 12 out of the way from interfering with eating or drinking.

With the concept of graduated length tampons, the nose bleed kit has particular utility for use by physicians who are more skilled in managing nose bleeds. Nose bleeds with bleeding sites more posterior could normally not be treated with a single tampon 10. Bleeding would continue because the single sponge would fail to exert any pressure on the more recessed bleeding site. The problem with prior art packings is that the placing of additional packing in the nose after the initial packing has been inserted is the possibility of pushing the initial pack too far back in the nasal cavity with the possibility of aspirating the packing. Prior art packings have dealt with this situation by utilizing a single extremely long tampon which always leaves a portion extending out of the nostril. Insertion of these long packings creates a comfort problem with the patient. With the graduated system of the present invention utilizing the multiple sponges, the sponges all share a common string which is anchored to the face thereby avoiding any problem of aspirating a sponge or leaving a sponge within the nose at the time of extraction. Also, the insertion of these string-connected oval-shaped sponges are easily inserted within the nasal cavity with little or reduced patient discomfort. The extremely long (9 centimeters) prior art sponges normally require some form of anesthesia before insertion of this rigid packing.

Figure 11:
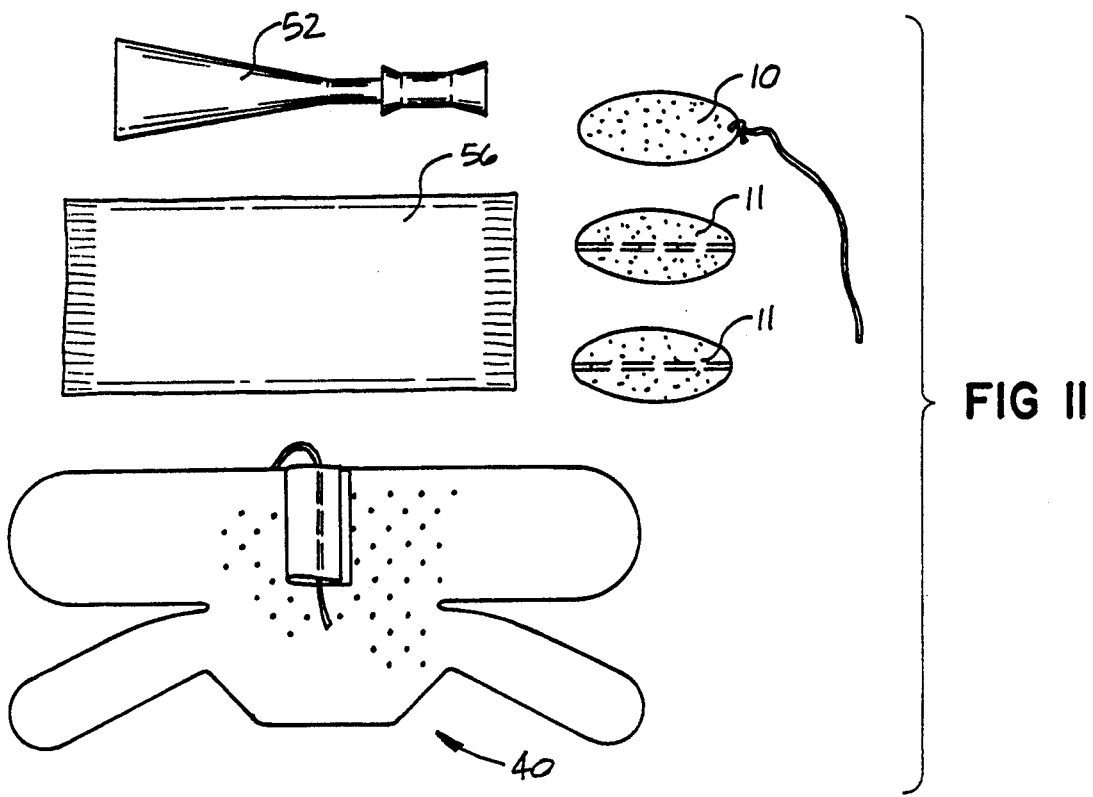
FIG. 11 is a plan view of the various components of the pre-packaged nose bleed kit of the present invention.

The kit of the present invention, as shown in FIG. 11, includes a tampon 10 with a string, two tampons 11 with passages for threading on a string 12, nasal bandage 40, packet 56 of antibiotic ointment and fluid dispenser 52 of a vasoconstrictive medication such as neosynephrine.

Figure 8:
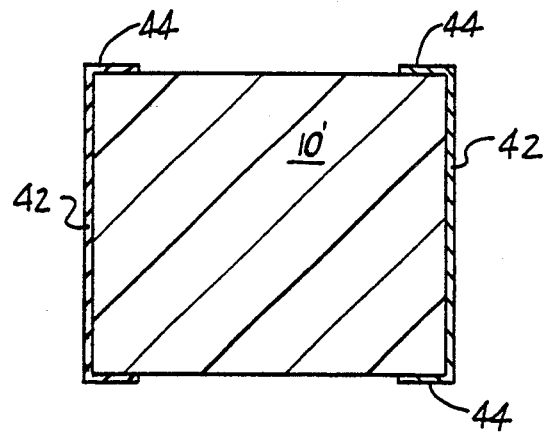
FIG. 8 is a similar view to FIG. 7 with the tampon in its expanded state.

FIGS. 7 and 8 illustrate lateral sectional views of a modified form of hemostatic tampon 10' to an enlarged scale having a similar oval shape to that of tampon 10 and 11. The tampon 10' is constructed of a similar compressed synthetic sponge material to that of FIG. 1 with the inclusion of a thin sheet 42 of collagen fibers surrounding the tampon 10'. This is accomplished by forming a circumferential groove 46 around the periphery of the tampon 10' and then taking two sheets 42 of collagen material and tucking the peripheral edges 44 within the circumferential groove 46 around its full periphery. When the tampon 10' is wetted and expands, the sheets of collagen 42 are expanded outward, as illustrated in FIG. 8, into contact with the bleeding areas within the nasal cavity. Tampon 11 can also be constructed in a similar fashion, a shown in FIGS. 7 and 8. Once the collagen sheets 42 are wetted, they will separate from expanded tampon 10' and upon tampon removal, the collagen 42 will remain in contact with the clotted blood on the interior surface of the nasal cavity.

Figure 9:
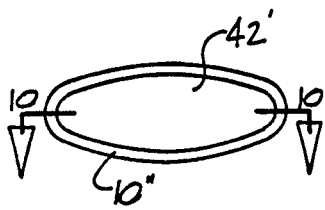
FIG. 9 is a plan view of a further form of modified hemostatic tampon.
Figure 10:
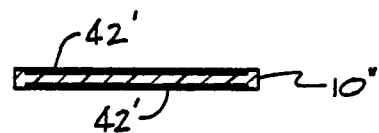
FIG. 10 is a longitudinal sectional view taken along lines 10—10 of FIG. 9.

Another modified form of tampon construction is shown in FIGS. 9 and 10 wherein a shallow cavity is cutaway on both sides of tampon 10" for receipt of a pair of thin sheets of collagen fiber 42' sized to fit the oval cavities in the tampon. Sheets 42' will likewise easily separate from the tampon 10" once the tampon has been expanded. The sheet 42 is produced under the brand name of HELISTAT by Marion Laboratories. Another form of collagen fiber is in powder form under the brand name AVITENE. The collagen fibers in powder form can be applied to the tampon by placing the fibers in a binder solution and then dipping the tampon in the binder. Collagen fibers function by trapping blood platelets resulting in more rapid clotting of the blood.

The sponge material utilized in the tampons could be any synthetic type hydrocellulose material which has good expansion ratios when expanded due to wetting from its compressed dry state.

It is understood that various modifications may be made in the hemostatic tampon shown and described herein, all within the scope of the invention. As for example, various other designs may be employed to attach the collagen fibers to the tampon either in power or sheet form.

Having described the invention with sufficient clarity to enable those familiar with the art to construct and use it, I claim:

1. A nose bleed kit comprising:
   at least a first hemostatic tampon constructed of a compressed synthetic sponge having rounded ends and a length approximately twice its width wherein said length is between 3 and 5 cm, sized for hand insertion without instruments within a nasal cavity and including a string attached thereto:
   a sealable container of liquid vasoconstrictive agent for wetting and expanding the sponge;
   a sealable container of anti-bacterial ointment for lubricating the sponge during insertion: and
   a bandage means having adhesive covered surfaces for attaching the string to a face of a user.

2. A nose bleed kit as set forth in claim 1, further including a second tampon similar in shape to the first tampon including a longitudinal passage means therethrough for receipt of said string to join and connect the first and second tampons.

3. A nose bleed kit as set forth in claim 1, including a thin sheet of collagen fiber wrapped around at least first tampon which readily separates from the at least first tampon once wetted.

4. A nose bleed kit as set forth in claim 1, wherein said at least first tampon is oval in plan view with a uniform thickness and has opposite planar sides with a shallow cavity in each side and thin sheets collagen fiber sized to fit within said cavities, respectively, positioned therein.

5. A nose bleed kit as set forth in claim 1, wherein said at least first tampon is substantially oval in plan view with a circumferential grove therearound, and further including a pair of thin sheets of collagen material sandwiching the at least first tampon therebetween with said sheets having peripheral edges which are tucked into said groove.

* * * * *

UNITED STATES PATENT OFFICE
CERTIFICATE OF CORRECTION

Patent No. 5,383,891              Dated  January 24, 1995

Inventor(s)  Marshall D. Walker

It is certified that error appears in the above-identified patent and that said Letters Patent is hereby corrected as shown below:

On the title page, item [54] and in column 1, line 2:

Correct the title of the patent to "NOSE BLEED KI_T_" instead of "NOSE BLEED KI_D_" as it currently appears.

Signed and Sealed this

Twenty-eight Day of March, 1995

Attest:

BRUCE LEHMAN

Attesting Officer      Commissioner of Patents and Trademarks